United States Patent [19]
Pearson et al.

[11] Patent Number: 5,769,858
[45] Date of Patent: Jun. 23, 1998

[54] LOCKING STYLET FOR EXTRACTING IMPLANTABLE LEAD OR CATHETER

[75] Inventors: Robert M. Pearson, Woodbury; Thomas C. Bischoff, Minneapolis; Brian Lee Fideler, Jordan, all of Minn.

[73] Assignee: Medtronic, Inc., Minneapolis, Minn.

[21] Appl. No.: 828,256

[22] Filed: Mar. 26, 1997

Related U.S. Application Data

[63] Continuation-in-part of Ser. No. 546,163, Oct. 20, 1995, abandoned.

[51] Int. Cl.[6] .................................................. A61F 11/00
[52] U.S. Cl. ............................ 606/108; 604/95; 600/585
[58] Field of Search ................................... 600/585, 146; 606/108, 159, 45, 129, 46, 47; 604/95

[56] References Cited

U.S. PATENT DOCUMENTS

| | | | |
|---|---|---|---|
| 3,910,279 | 10/1975 | Okada et al. | 606/46 |
| 4,106,512 | 8/1978 | Bisping | 128/418 |
| 4,217,913 | 8/1980 | Dutcher | 128/785 |
| 4,471,777 | 9/1984 | McCorkle, Jr. | 128/303 |
| 4,574,800 | 3/1986 | Peers-Trevarton | 128/303 R |
| 4,576,162 | 3/1986 | McCorkle | 128/303 |
| 4,582,056 | 4/1986 | McCorkle, Jr. | 128/303 |
| 4,886,074 | 12/1989 | Bisping | 128/785 |
| 4,917,106 | 4/1990 | Olivier | 128/785 |
| 4,953,564 | 9/1990 | Berthelsen | 128/784 |
| 4,967,766 | 11/1990 | Bradshaw | 128/785 |
| 4,988,347 | 1/1991 | Goode et al. | 606/1 |
| 5,002,067 | 3/1991 | Berthelsen et al. | 128/786 |
| 5,011,482 | 4/1991 | Goode et al. | 606/1 |
| 5,013,310 | 5/1991 | Goode et al. | 606/1 |
| 5,024,617 | 6/1991 | Karpiel | 606/46 |
| 5,207,683 | 5/1993 | Goode et al. | 606/108 |
| 5,261,419 | 11/1993 | Osypka | 607/122 |
| 5,304,131 | 4/1994 | Paskar | 604/95 |
| 5,396,902 | 3/1995 | Brennen et al. | 600/585 |
| 5,409,453 | 4/1995 | Lundquist et al. | 604/22 |
| 5,423,806 | 6/1995 | Dale et al. | 606/14 |
| 5,439,006 | 8/1995 | Brennen et al. | 600/585 |
| 5,441,483 | 8/1995 | Avitall | 604/95 |

*Primary Examiner*—Robert A. Hafer
*Assistant Examiner*—Justine R. Yu
*Attorney, Agent, or Firm*—Thomas F. Woods; Harold R. Patton

[57] ABSTRACT

Disclosed is a locking stylet for extracting elongate, body-implantable leads or catheters having a lumen disposed therewithin. A tubular member of the present invention has an outer diameter "A" sufficiently small to permit its insertion in the lumen of a lead or catheter, and additionally has an aperture formed in the sidewall thereof at a point near the distal end thereof. A pull wire is affixed to the distal end of the tubular member through the lumen and extends slightly beyond the proximal end of the tubular member. A tractional force imparting mechanism is coupled to the proximal end of the pull wire for exerting a tractional force on the pull wire. Tractional force is transferred by the pull wire to the distal end of the tubular member and causes the distal end of the tubular member to permanently deform, sharply bend or kink at a point located beneath the aperture. The kinking action of the tubular member increases its maximum cross-sectional diameter at the distal end and thereby causes the distal end thereof to forcefully engage the sidewall of the lead or catheter lumen.

76 Claims, 11 Drawing Sheets

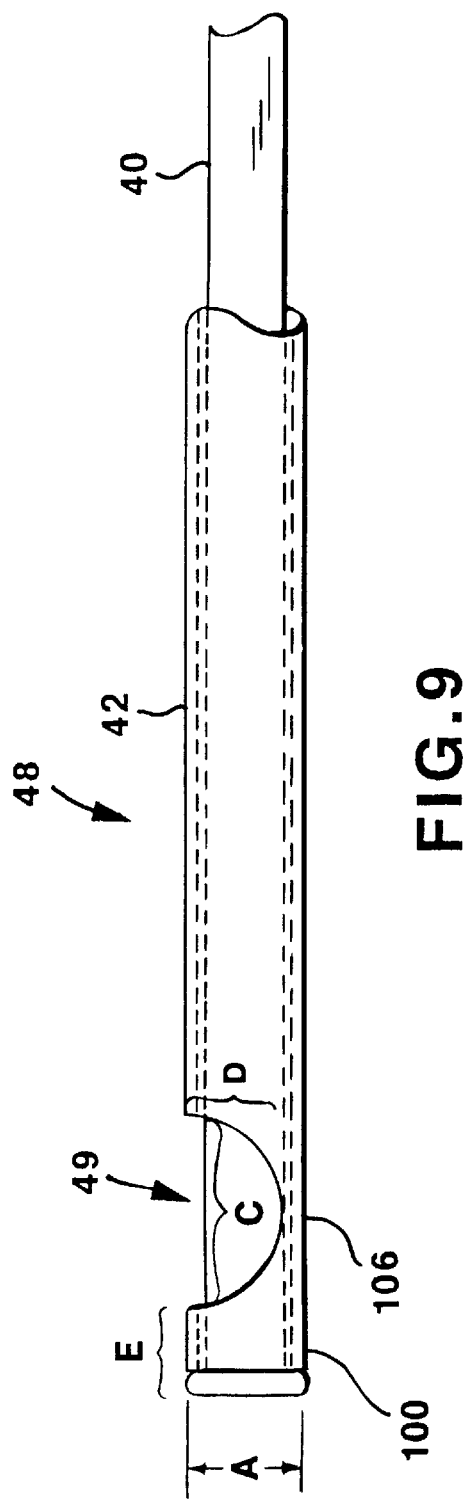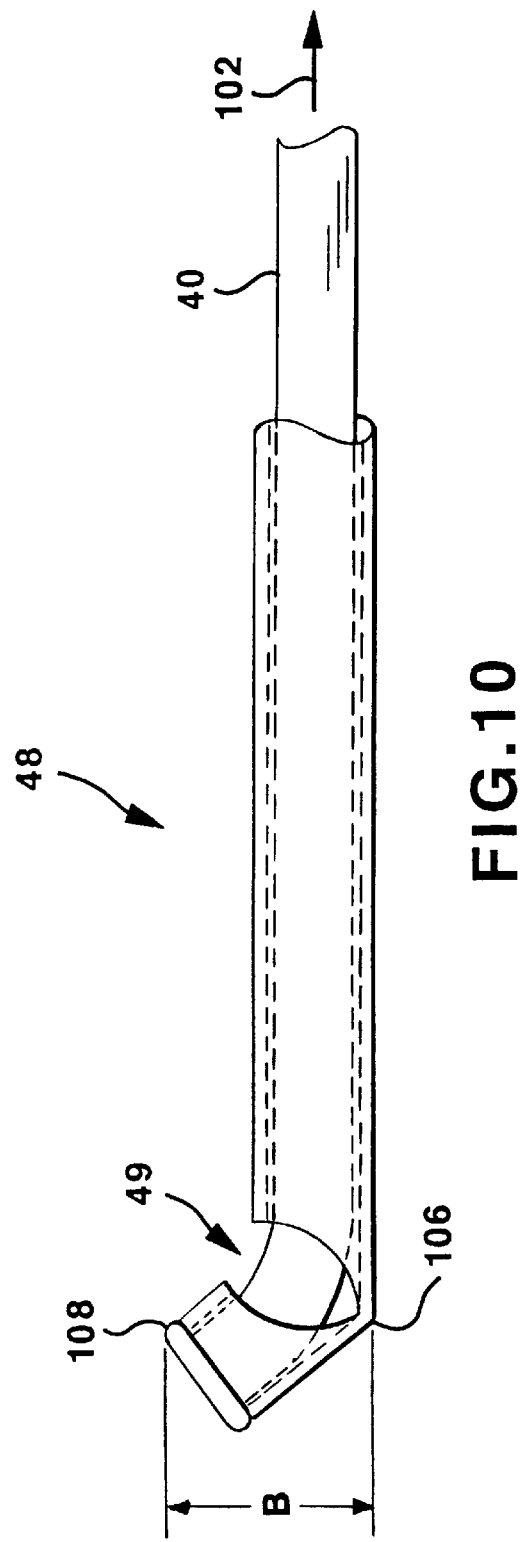

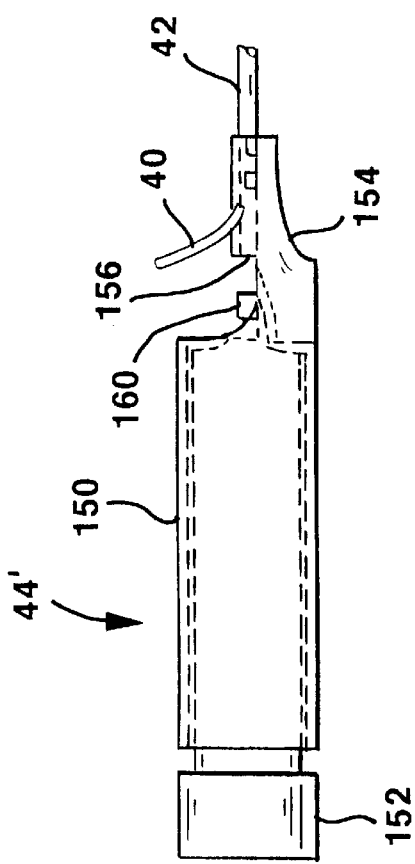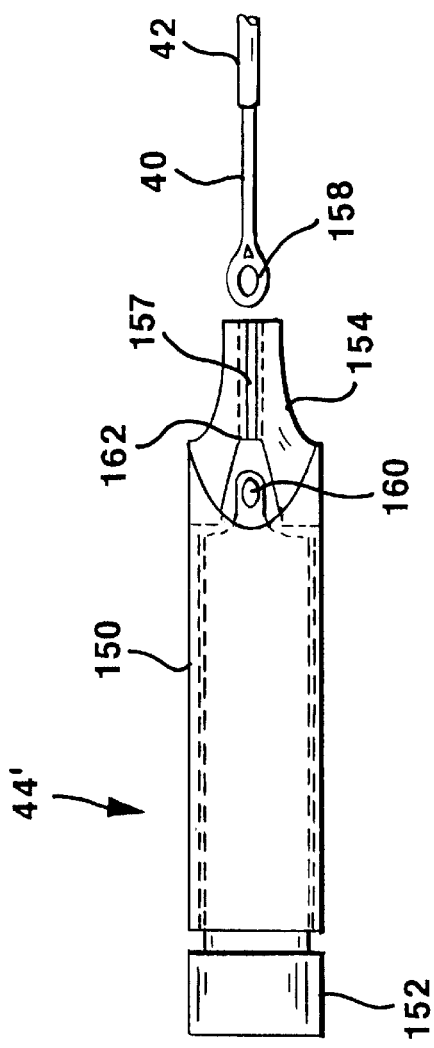
FIG.12
FIG.13

LOCKING STYLET FOR EXTRACTING IMPLANTABLE LEAD OR CATHETER

This application is a continuation-in-part of application Ser. No. 08/546,163, filed Oct. 20, 1995, now abandoned.

FIELD OF THE INVENTION

This invention relates to the field of body-implantable leads, and more particularly relates to a method and apparatus for removal of chronically-implanted leads, catheters and the like from a patient.

BACKGROUND OF THE INVENTION

Various types of body-implantable leads and electrodes are known in the prior art for use in connection with automatic, body-implantable medical devices such as cardiac pacemakers, cardiac defibrillators, cardioverters, neural stimulators and the like. Implantable leads typically include a flexible, elongate insulating sheath or sleeve of, for example, polyurethane, surrounding one or more conductors extending between the proximal and distal ends of the lead. The internal conductors of an implantable lead are frequently disposed in a coiled configuration to define a lumen that extends throughout the length of the lead body. The coiled configuration of the lumen advantageously contributes to the flexibility and durability of the lead.

The lumen of a lead may also enable a stiffening wire or stylet to be inserted in the lumen to impart rigidity and steerability to the lead during implantation. After implantation, the stylet is withdrawn to render the lead flexible. See, for example, U.S. Pat. No. 5,439,006 to Brennan et al. entitled "Steerable Stylet and Manipulative Handle Assembly", where such a steerable stylet is disclosed.

Endocardial leads generally have one or more electrodes disposed near their distal ends for positioning in a chamber or portion of the heart such as the right atrium, right ventricle, the right atrial appendage or the coronary sinus.

Lead electrodes are placed in contact with myocardial tissue by passage of the lead through a vein such as the subclavian vein or one of its tributaries. The tip of the lead is typically held in place by trabeculae present in the myocardial tissue. A fixation mechanism is often provided at the distal end of the lead to enhance the chronic stability of lead positioning and electrode placement.

Among the many available types of leads are those having either "active fixation" or "passive fixation" mechanisms. Known passive fixation mechanisms include flexible tines, wedges, or finger-like projections that extend radially outward and usually are molded from and/or are integral with the insulating sheath of the lead. These tines or protrusions allow surrounding growth of tissue and scar in chronically implanted leads to fix the electrode tip in position in the heart and prevent dislodgment of the tip during the life of the lead.

In "acute placement" of an electrode (i.e., during the period of time immediately following lead implantation) a blood clot typically forms about the flanges or tines until scar tissue forms. The tines, wedges or finger-like projections allow better containment by the myocardial trabeculae and prevent early dislodgment of the lead tip. An example of a tined lead is shown in U.S. Pat. No. 4,917,106 to Olivier, entitled "Conductive Tips of Cardiac Stimulation Probes."

Known types of active fixation mechanisms for cardiac leads include "screw-in" tips in which a sharpened helical or "corkscrew" needle is provided at the distal end of the lead for engaging myocardial tissue. In some prior art screw-in leads, the helical needle is capable of being screwed in to endocardial tissue by means of a slotted-tip or screwdriver-tip stylet which is inserted into the lead during the implantation process and rotated at its proximal end to secure the distal end in place. Examples of screw-in leads are described in U.S. Pat. No. 4,886,074 to Bisping, entitled "Implantable Lead Assembly With Extendable Screw-In Electrode;" in U.S. Pat. No. 4,217,913 to Dutcher, entitled "Body-Implantable Lead With Protected, Extendable Tissue Securing Means;" in U.S. Pat. No. 4,967,766 to Bradshaw, entitled "Implantable Endocardial Lead With Fixation Apparatus Retractable by a Lanyard;" in U.S. Pat. No. 4,106,512 to Bisping, entitled "Transvenously Implantable Lead;" in U.S. Pat. No. 4,953,564 to Berthelsen, entitled "Screw-In Drug Eluting Lead;" and in U.S. Pat. No. 5,002,067 to Berthelsen et al., entitled "Medical Electrical Lead Employing Improved Penetrating Electrode."

Although the state of the art in implantable pulse generator or pacemaker technology and endocardial lead technology has advanced considerably, endocardial leads nevertheless occasionally fail. Failure can occur for a variety of reasons, including breakage of a lead, insulation breaks, breakage of the inner helical coil conductor thereof, and increases in electrode resistance. Upon failure of an implanted lead, it may in some cases, as for example in pacemaker-dependent patients, become necessary to implant a replacement lead. Replacement leads may also be required in situations where it is desired to stimulate a different endocardial site than that stimulated with an existing lead.

Although it would be desirable to be able to easily remove a failed or unused lead prior to implanting a replacement lead, in the past surgeons have avoided attempts to remove inoperative leads because the risk of removing such leads often exceeded the risk of leaving such leads implanted. Thus, there are a considerable number of patents who have one or more, and sometimes as many as four or five, unused leads disposed in their veins and heart.

The risks of leaving unused myocardial leads in the heart and venous pathways include an increased likelihood that an old lead will become the site of infection. Such infections, in turn, sometimes necessitate removal of a lead to prevent continued bacteremia and abcess formation which, in turn, may lead to fatal complications. Furthermore, there is an increased likelihood of the formation is of blood clots in the atrial chamber about entangled leads. Such clots may cause embolisms in lung tissue and produce severe complications or even death. Moreover, the presence of unused leads in a venous pathway or inside the heart may cause considerable difficulty in the positioning and attachment of new endocardial leads in the heart. The potential for infection and other complications increases rapidly as a number of old or unused endocardial leads in the heart and venous pathway increases.

Removal of an inoperative lead sometimes can be accomplished by applying tractional force and rotation to the proximal end of the lead. This method is most effective, however, when done prior to fixation of the lead tip in the trabeculae by scar formation or large clot development. Even then, clots may have formed, causing increased risk to attend lead removal due to emboli potentially passing to the lungs, where severe complications may ensue.

In cases where the lead tip has become attached by scar tissue to the myocardial wall, removal of the lead may present major problems and risks. This is particularly true for porous lead tips, such as that disclosed in U.S. Pat. No. 4,506,680 to Stokes. Porous lead tips may exhibit an in-growth of scar tissue attached to the myocardial wall. The application of sufficient tractional force on such leads during removal may cause excessive disruption and displacement of the myocardial wall before the embedded lead tip is released, and can lead to death.

The tines or flanges characteristic of other types of leads that do not become tightly secured to the myocardial wall by scar tissue may present similar risks. Even if screw-in leads of the kind mentioned above are employed, unscrewing of such tips may be prevented by a channel of scar tissue or endothelium surrounding the outer surface of the lead along the venous pathway. Such "channel scar" tissue may prevents lead withdrawal owing to tight encasement of the lead tip. Continual strong pulling or twisting of the outer free end of the lead may cause rupturing of the right atrial wall or right ventricular wall under such circumstances. Such tight encasement by scar tissue in the venous pathway and in the trabeculae of the myocardial wall typically occurs within six months to one year of initial lead implantation.

Another problem concerning removal of implanted leads through the application of pulling force upon the proximal end is that the flexible sheath of the lead body can stretch and possibly tear under the applied tractional force. This is especially true for leads which have been implanted for long periods of time, since exposure to the harsh in vivo environment may cause the sheath to deteriorate over time. If the lead body tears, there is a risk that portions of the lead will become detached, seriously complicating the lead removal procedure.

The risks attending lead removal by tractional force and rotation of the lead may be so great that a surgeon may elect to open a patient's chest and surgically remove the lead rather than attempt removal by conventional tractional force means.

To address the foregoing problems, there have been various tools and methods for lead removal proposed in the prior art. U.S. Pat. No. 4,471,777 to McCorkle, Jr., entitled "Endocardial Lead Extraction Apparatus and Method," for example, proposes a three-catheter lead removal system, wherein a first catheter, described as having a "lead grasping" mechanism is attached to a free end of a lead. Second and third catheters, concentrically disposed around the first catheter, are then advanced along the lead body to separate adherent scar tissue from the surface of the lead along its length and at its tip.

U.S. Pat. No. 4,574,800 to Peers-Travarton, entitled "Implanted Lead Extractor," appears to propose an extraction assembly including an elongate tubular member having a length of line running along its length. The extraction assembly is configured to be inserted into the longitudinal lumen of an implanted lead, and is provided with a mechanism for being radially expanded at its distal end. Once the assembly is inserted into the lead, its radial end is expanded and the extraction assembly and lead are withdrawn from the heart and vein as a unit. In this way, tractional force is advantageously applied at or near the distal end of the lead.

In U.S. Pat. No. 4,988,347 to Goode et al., entitled "Method and Apparatus for Separating a Coiled Structure From Biological Tissue," there is proposed an extraction tool comprising a stylet wire with an expandable wire coil attached to its distal end. When the stylet is inserted into the lead's internal lumen, the wire coil is rotated to expand its coils and engage the lead at or near its distal end. A somewhat similar arrangement is described in U.S. Pat. No. 5,013,310 to Goode et al., entitled "Method and Apparatus for Removing an Implanted Pacemaker Lead," in U.S. Pat. No. 5,011,482 to Goode et al., entitled "Apparatus for Removing an Elongated Structure from Biological Tissue," and in U.S. Pat. No. 5,207,683 to Goode et al., entitled "Apparatus for Removing an Elongated Structure Implanted in Biological Tissue."

Another implantable lead extraction arrangement is proposed in U.S. Pat. No. 5,261,419 to Osypka, entitled "Cardiac Pacemaker Lead." The lead described in the Osypka '419 patent includes a chamber at its distal end, this chamber housing a coupling element engaged by a complementary coupling element disposed on the end of an extraction stylet.

To further facilitate the extraction of ingrown leads that cannot simply be pulled out, there have been proposed in the prior art numerous types of so-called "cutting catheters." Cutting catheters are adapted to separate and/or dislodge a lead whose tip is embedded in scar tissue, such that excessive forces are not necessary to accomplish lead extraction. Cutting catheter systems are discussed, for example, in U.S. Pat. No. 4,582,056 to McCorkle, Jr., entitled "Endocardial Lead Extraction Apparatus and Method;" U.S. Pat. No. 4,576,162 to McCorkle, entitled "Apparatus and Method for Separation of Scar Tissue in Venous Pathway;" U.S. Pat. No. 4,471,777 to McCorkle, entitled "Endocardial Lead Extraction Apparatus and Method."

A lead extraction device that utilizes laser light to separate an implanted lead from fibrous scar tissue is disclosed in U.S. Pat. No. 5,423,806 to Dale et al., entitled "Laser Extractor for an Implanted Object." The laser extractor described in the Dale et al. '806 patent features a catheter having a central lumen dimensioned so a pacemaker lead will fit therein. In use, the catheter is guided by the lead along the venous pathway of the lead. The laser catheter has at least one optical fiber to emit laser light from a distal end and thereby separate the lead from fibrous scar tissue. The Dale et al. laser catheter may emit laser light both parallel to the lead and inwardly perpendicular to the lead, such that the lead may be separated along its length and at its distal end from fibrous scar tissue.

The above-identified McCorkle '056, '162, and '777 patents and the Dale et al. '806 patent are each hereby incorporated by reference herein in their respective entireties.

Notwithstanding the foregoing and other prior art proposals for lead extraction, there exists a need for improving lead extraction tools and methods. For example, the extraction tool required to explant a particular type of lead is often unique to that particular type of lead. That is, a different tool may be necessary for each different type or style of lead, even as among different leads provided by the same manufacturer.

Additionally, many prior art extraction tools require customization or cutting-to-length on a patient-to-patient basis. Such customization usually must be performed contemporaneously with, rather than prior to, the explant procedure. This tends to undesirably complicate and prolong the explant procedure.

SUMMARY OF THE INVENTION

In view of the foregoing considerations, the present invention is directed to an improved method and apparatus for the extraction of elongate leads that provides reduced risk to patients.

More particularly, the present invention is directed to a tubular member or stylet for providing a relatively large tractional force to a predetermined, localized portion of an implanted lead. The tubular member or stylet of the present invention permits a relatively large force to be applied to the tip of a lead encased in fibrotic growth, tissue or tribeculae without breaking the lead. This large tractional force is applied to the distal end of the lead through the distal tip of the tubular member of the present invention by a pull wire. An aperture disposed near the distal tip of the tubular member causes the distal tip of the tubular member to kink in response to the tractional force applied by the pull wire. The kinked tip then forcefully engages the sidewall of the lead lumen at the distal end thereof and within which the tubular member is disposed.

A large tractional force is applied only to the distal tip of the lead where encasement of the lead distal tip by tissue or fibrotic growth generally occurs, thereby permitting relatively easy and quick lead extraction while imparting minimum trauma to the myocardium. The present invention thus permits a physician to spend a reduced amount of time removing a lead from a patient's heart while simultaneously reducing the degree of trauma imparted to heart tissue.

The present invention also permits implanted leads to be removed from a patient without stretching, tearing or breaking the flexible sheath of a lead body while nevertheless applying a relatively large tractional force to the tip of the implanted lead.

In accordance with another feature of the present invention, a method and apparatus is provided for allowing placement of new endocardial leads and electrodes without interference by old leads in the venous path or heart with the new leads. In accordance with another aspect of the invention, a method and apparatus is provided for removal of infected leads without the need for open chest surgery. Other objects, features and advantages of the present invention will become apparent upon referring to the drawings and specification hereof.

BRIEF DESCRIPTION OF THE DRAWINGS

The foregoing and other aspects of the present invention will perhaps be best appreciated with reference to the following detailed description of the preferred embodiments of the present invention and accompanying drawings, where:

FIG. 9 is an enlarged side view of a distal portion of the locking stylet of FIG. 2 in an unarticulated position;

FIG. 10 is an enlarged side view of a distal portion of the locking stylet of FIG. 2 in an articulated position;

FIG. 12 is a side, cross-sectional view of an alternative embodiment of a manipulable handle assembly for the locking stylet of FIG. 2;

FIG. 13 is a top, cross-sectional view of the manipulable handle assembly from FIG. 12;

DETAILED DESCRIPTION OF THE PREFERRED EMBODIMENTS

In the specification and claims hereof, the term "lead" is used in its broadest sense and includes within its scope a stimulation lead, a sensing lead, any combination thereof, or any other elongate member, such as a catheter, which may usefully be introduced or implanted into a body.

Figure 1:
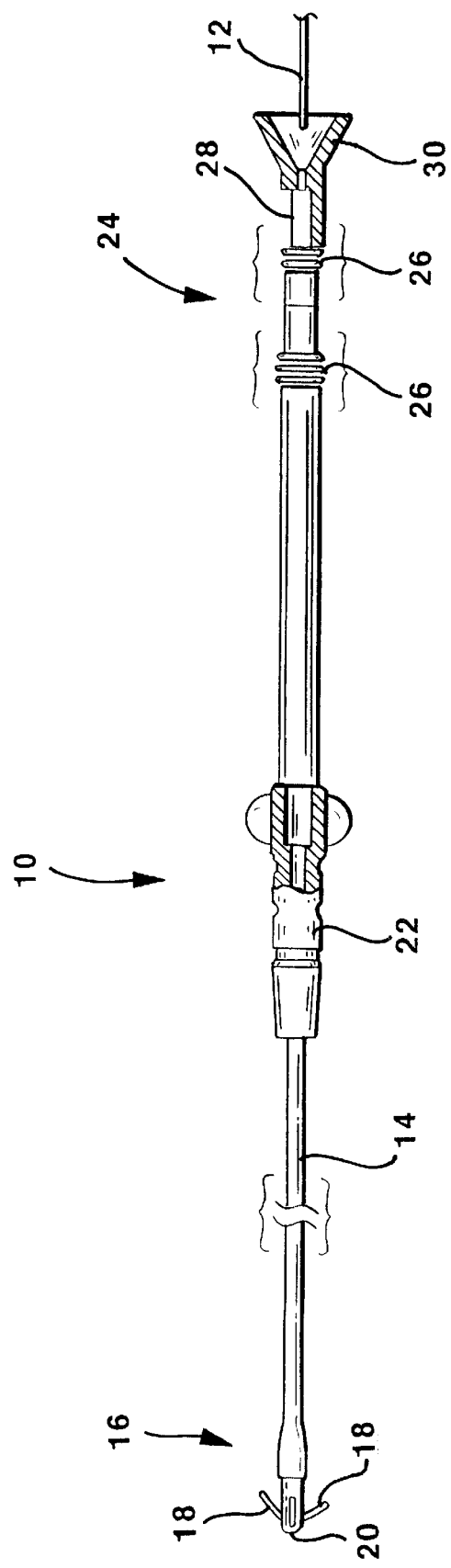
FIG. 1 is a side view of a body-implantable lead having a locking stylet inserted therein.

FIG. 1 shows a prior art body-implantable cardiac pacing/sensing lead 10. Also shown in FIG. 1 is a universal locking stylet 12 in accordance with one embodiment of the present invention, locking stylet 12 being shown in FIG. 1 having been inserted at the proximal end of lead 10 into an inner lumen of lead 10.

Although the present invention is described herein in the context of the extraction of a cardiac pacing sensing lead from a patient, it is contemplated that the present invention may be advantageously practiced in connection with the extraction of other types of elongate, body-implantable devices such as, for example, catheters and the like.

Lead 10 comprises an elongate lead body 14 and a tip electrode assembly, designated generally by reference numeral 16 in FIG. 1, disposed at the distal end of lead body 14. (Only the distal section of elongate lead body 12 is shown in FIG. 1.)

As shown in FIG. 1, lead 10 is of the so-called passive-fixation type, having a plurality of pliant barbs or "tines" 18 disposed generally at or near the distal end of lead 10. Tines 18 are employed in accordance with known practice to engage the trabeculae within the heart chamber, providing lead fixation to ensure stable contact between tip electrode 20 and endocardial tissue.

As noted above, although lead 10 in the disclosed illustrative embodiment is of the tined, passive-fixation type, this is not a necessary or essential aspect of the present invention. Those of ordinary skill in the art having the benefit of the present disclosure will appreciate that the present invention may be advantageously practiced in connection with leads of either the active- or passive-fixation variety.

Lead body 14 is covered by an insulative sleeve of flexible biocompatible and biostable insulating material, such as polyurethane or silicone rubber. At the proximal end of lead 10, a terminal assembly designated generally as 24 is provided for coupling lead 10 to an implantable pulse generator (not shown). Terminal assembly 24 is provided with sealing rings 26 and a terminal pin 28, all of a type known in the art. An anchoring sleeve 22 (shown partially in cross-section) may also be provided on lead body 14. Anchoring sleeve 22 slides over lead body 14 and serves as a point for suturing lead body 14 to body tissue at the insertion point of lead 10 in a fashion known in the art. Anchoring sleeve 22 and terminal assembly 24 are preferably fabricated from silicone rubber, although they may also be constructed of any other suitable biocompatible material known in the art.

Lead 10 shown in FIG. 1 may also include a stylet guide 30 for facilitating insertion of a stylet, such as locking stylet 12, into an internal lumen of lead 10, as would be familiar to those of ordinary skill in the art. Locking stylet 12 is preferably provided with a knurled knob for enabling stylet 12 to be maneuvered through the internal lumen of lead 10.

Figure 2:
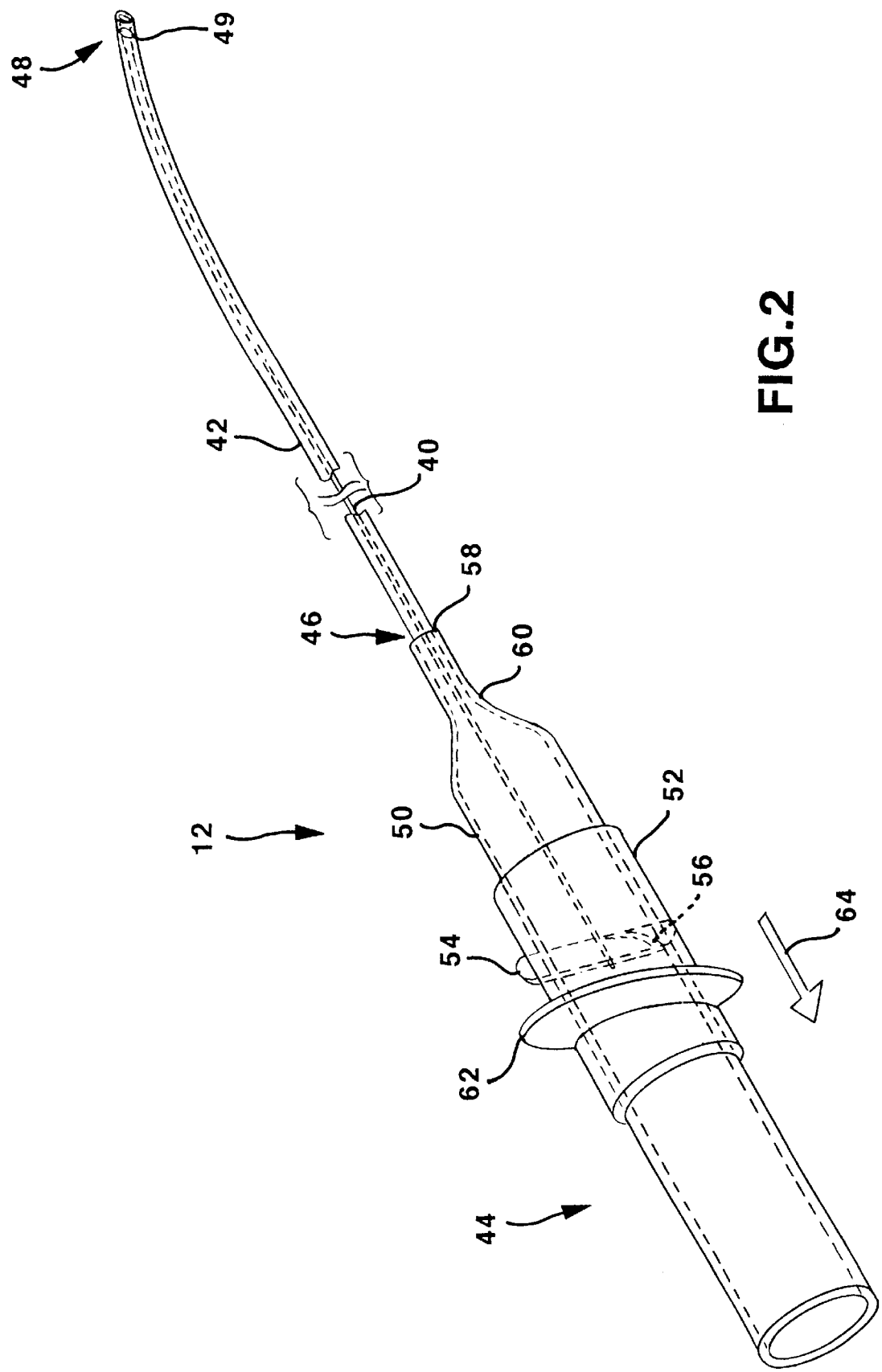
FIG. 2 is an enlarged perspective view of the locking stylet of FIG. 1.

FIG. 2 shows an enlarged, partially cut-away side view of locking stylet 12 in accordance with one embodiment of the invention. As shown in FIG. 2, locking stylet 12 comprises an inner pull wire 40 disposed within the generally cylindrical lumen of an outer, elongated tubular member 42. A manipulable handle assembly, designated generally with reference numeral 44, is disposed at the proximal end 46 of tubular member 42. Pull wire 40 extends along the entire length of tubular member 42, and is fixedly coupled at its distal end to the distal end 48 of tubular member 42.

As is hereinafter described in greater detail, aperture 49 is formed in tubular member 42 near distal end 48 thereof. For the sake of clarity, the intermediate section of locking stylet 12 is not shown in FIG. 2. Those of ordinary skill in the art will appreciate, however, that locking stylet 12 is most preferably long enough to extend along the entire length of conventional body-implantable leads.

Manipulable handle assembly 44 attached to proximal end 46 of tubular member 42 includes a (preferably cylindrical) housing 50, a slide member 52, a lever 54, and a spring wire clip element 56. In particular, tubular member 42 is mechanically attached to an opening 58 in tapered neck portion 60 of housing 50 and is mechanically coupled to lever 54 as illustrated more completely in FIGS. 3 and 4. Manipulable handle assembly 44 may be removably attached to elongated tubular member 42, thereby permitting manipulable handle assembly 44 to be reusable in conjunction with disposable tubular members 42 and pull wires 40.

Tubular member 42 and pull wire 40 are inserted into terminal pin 28 of lead 10 which is axially arranged with the lumen within the lead body, in accordance with conventional lead design. The overall dimensions of housing 50 and slide member 52 are configured to fit within a physician's hand so as to allow thumb engagement with a circular ridge 62 on slide member 52 to move slide member 52 with respect to housing 50 (i.e., in the direction of arrow 64 in FIG. 2).

Figure 3:
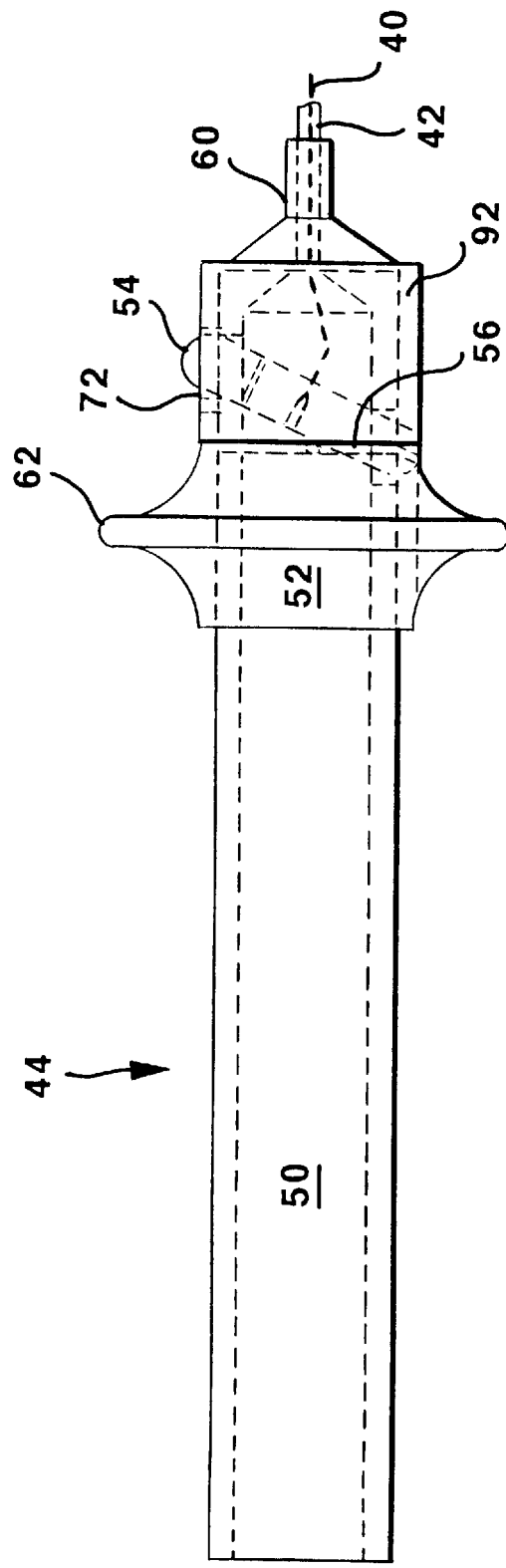
FIGS. 3 and 4 are enlarged side views of the manipulable handle assembly of the locking stylet of FIG. 2 with a sliding assembly in relaxed and fully tractioned positions, respectively.
Figure 4:
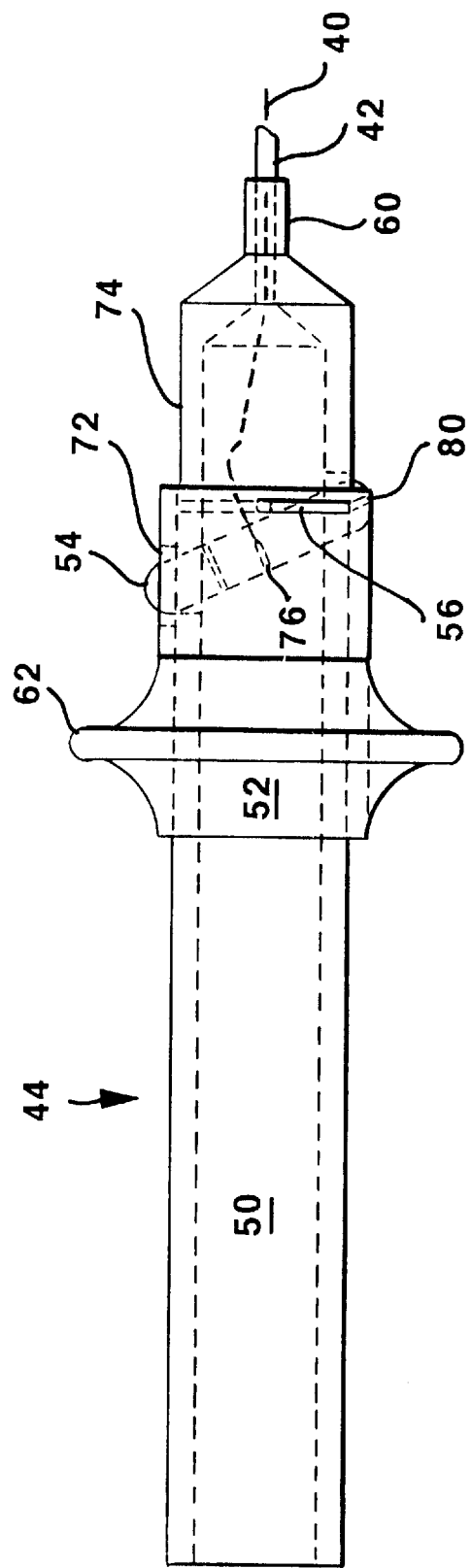
Figure 7:
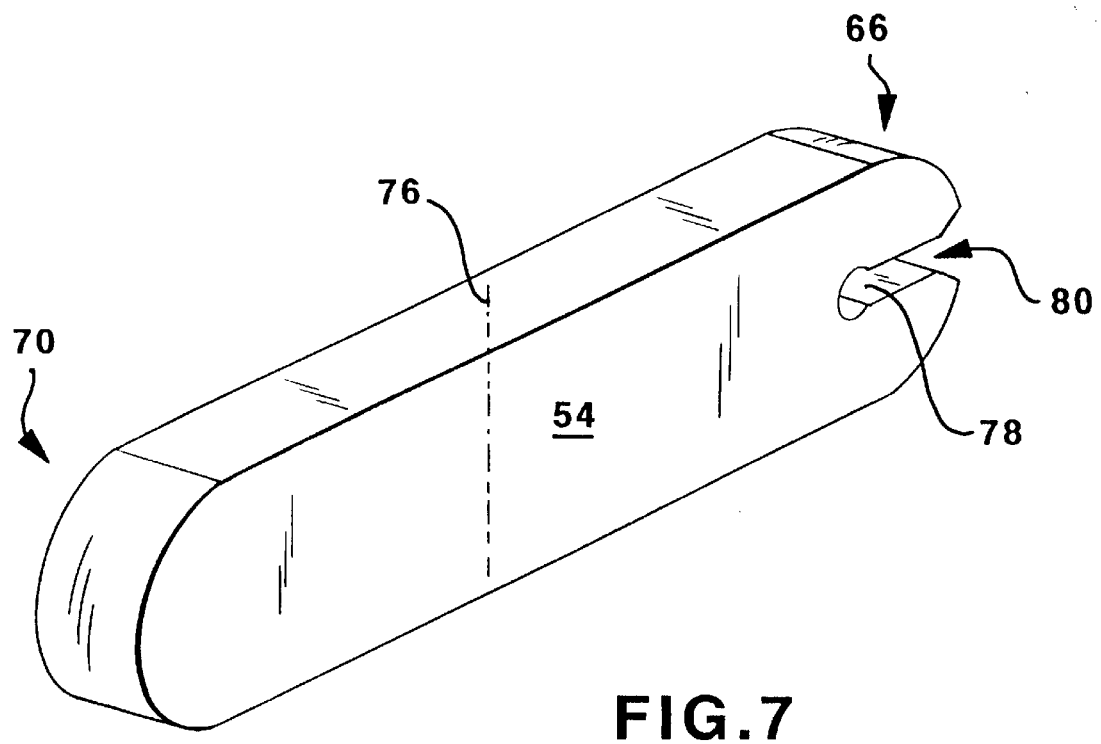
FIG. 7 is an enlarged perspective view of a lever element in the manipulable handle assembly of FIGS. 3 and 4.

FIGS. 3 and 4 show side elevation, phantom line views of manipulable handle assembly 44 in the relaxed and fully tractioned positions, respectively. The positions of slide member 52 and lever 54 in relation to housing 50 are also illustrated. Lever 54, shown in FIG. 7, is pivoted at its fixed end 66 on clip 56, and is pivoted at its free end 70 by slot 72 in the top surface of slide member 52. Lever 54 is pivoted back and forth by movement within an elongated channel 74 in housing 50. The proximal end of pull wire 40 is fitted in an opening 76 along the body of lever 54 so that it is pulled back with movement of slide member 52 in the direction of arrow 64 (see FIG. 2).

Figure 5:
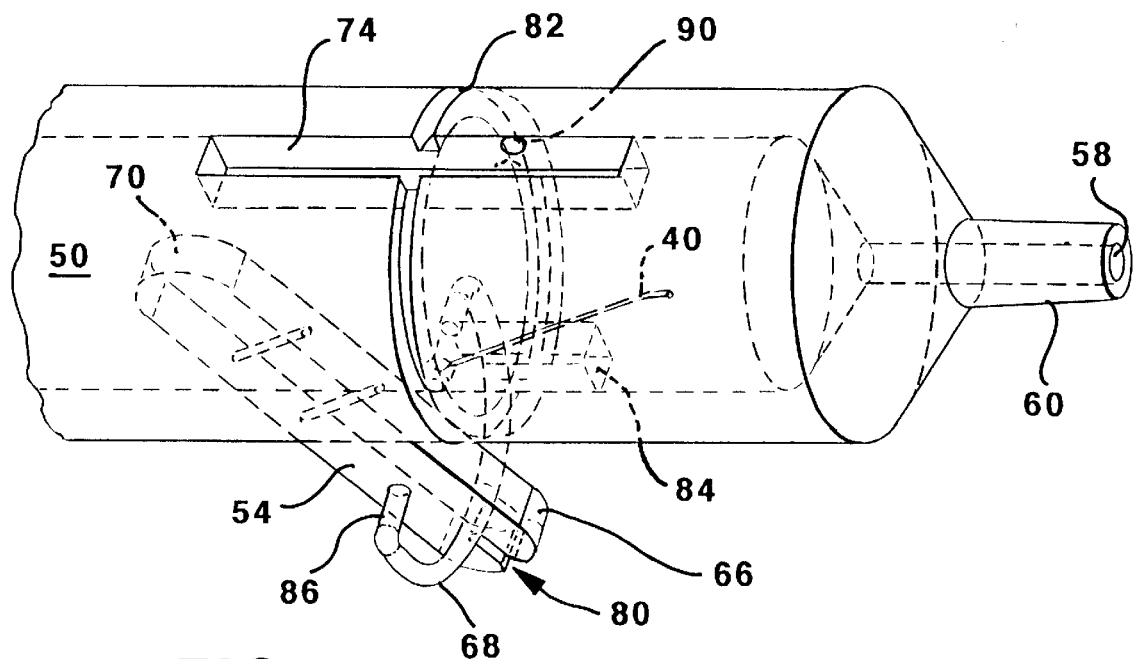
FIG. 5 is an enlarged perspective view of a portion of the manipulable handle assembly of FIGS. 3 and 4.

FIG. 5 shows a perspective view of housing 50 and illustrates the manner in which lever 54 and clip 68 are connected to the proximal end of pull wire 40. Lever 54, as shown in FIG. 7, is a flat-sided elongate member having a pair of semicircular-shaped ends 66 and 70. Clothes-pin shaped hole 78 and groove 80 in fixed end 66 thereof are slipped over clip 68.

Figure 6:
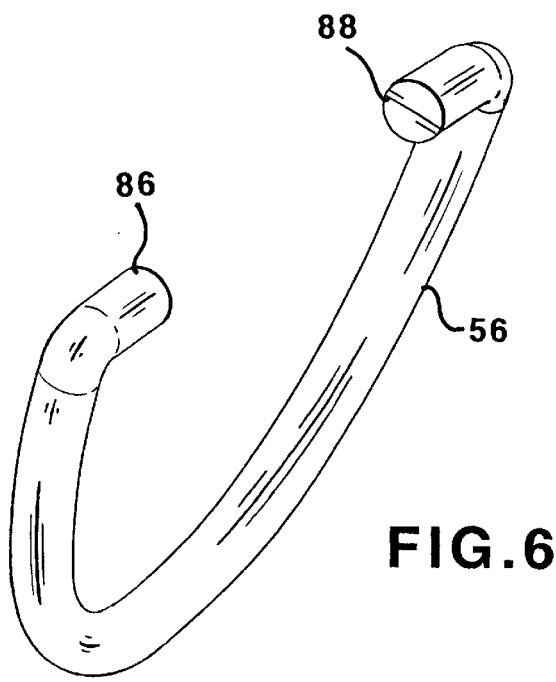
FIG. 6 is an enlarged perspective view of a clip element in the manipulable handle assembly of FIGS. 3 and 4.

Clip 56, shown in FIG. 6, is generally C-shaped, and is adapted to fit within a wrap about the circumference of groove 82 extending across bottom opening 84 in housing 50. Bottom opening 84 receives the end of lever 54 which snaps onto clip 68 by action of groove 82. The shape and springiness of clip 68 retains it in position once ends 86 and 88 of clip 68 are snapped into groove 82 and holes 90 on each side of housing 50. Similarly, lever 54 is snapped into place so that hole 78 fits around the exposed portion of clip 68 traversing bottom opening 84 of housing 50. Elongated channel 74 in housing 50 extends a distance sufficient to provide the desired degree of movement of lever 54 and pull wire 40 with regard to tubular member 42.

Figure 8:
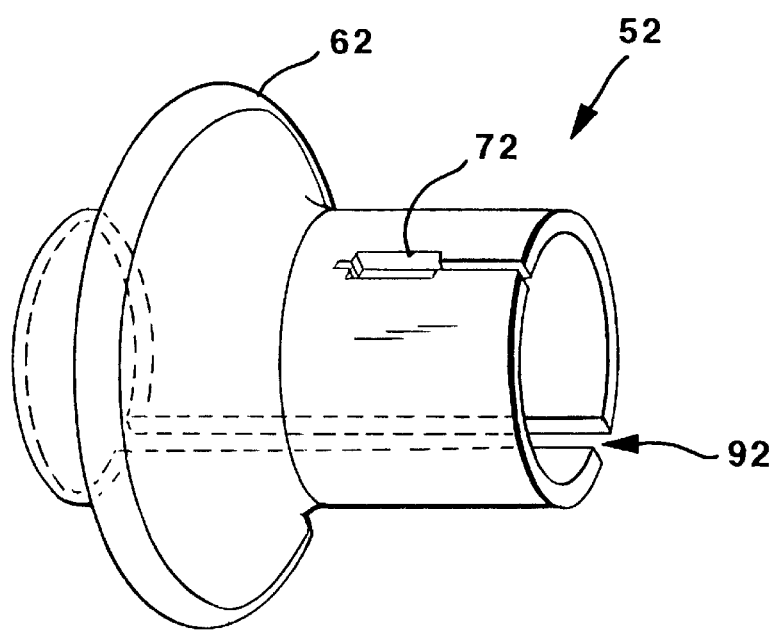
FIG. 8 is an enlarged perspective view of a sliding member in the manipulable handle assembly of FIGS. 3 and 4.

FIG. 8 shows a perspective view of slide member 52. Slot 72 receives free end 70 of lever 54 and permits movement thereof back and forth within channel 74 and opening 92. See also FIGS. 3 and 4. Manipulable handle assembly 44 described hereinabove permits manipulation of free end 70 of lever 54 to thereby draw end 70 in a proximal direction in respect of tubular member 10, and causes pull wire 40, also coupled to lever 54, to be drawn in a proximal direction.

FIG. 9 shows a portion of locking stylet 12 comprising distal portion 48, tubular member 42 and pull wire 40. In the embodiment of the present invention shown in FIG. 9, tubular member 42 is most preferably formed of stainless steel tubing similar to conventional hypodermic needle material, where dimension "A", the outer diameter of the tubing, is most preferably about 0.016 inches. Dimension "A" may also range between about 0.75 inches and about 0.006 inches, between about 0.50 inches and about 0.010 inches, between about 0.25 inches and about 0.012 inches, between about 0.20 inches and about 0.14 inches, or between about 0.18 inches and about 0.15 inches. Tubular member 42 most preferably has an outer diameter "A" sufficiently small that it may be inserted in the lumen of a conventional body-implantable lead or catheter. That is, dimension "A" should be sufficiently small that tubular member 42 fits within the lumen of the tubular lead or catheter that is to be removed.

In preferred embodiments of the present invention, aperture 49 in FIG. 9 is disposed in a region ranging between about 0.006 to about 1.0 inch, or between about 0.010 to about 0.50 inches, or between about 0.012 to about 0.30 inches, or between about 0.014 inches to about 0.10 inches, or between about 0.016 inches to about 0.075 inches, or between about 0.018 inches to about 0.050 inches, or between about 0.020 inches to about 0.042 inches in a proximal direction from the extreme distal end of stylet 12, where those ranges of length are defined according to dimension "E" in FIG. 9. Dimension "E" in FIG. 9 most preferably ranges between about 0.016 inches and about 0.042 inches.

Alternatively, dimension "E" in FIG. 9 may be expressed in respect of its relation to dimension "A". More particularly, in preferred embodiments of the present invention, dimension "E" should range between about ⅛ and about 3 times dimension "A", between about ¼ and about 2 times dimension "A", or between about ½ and about 1 times dimension "A". It is preferred that dimension "E" be 1 to 3 times greater than dimension "A".

Pull wire 40 is most preferably made of 0.007-inch diameter MP35N chromium-nickel alloy wire, although any other suitable type or size of biocompatible and sufficiently strong wire may be employed in the present invention. Pull wire 40 must have an outer diameter sufficiently small that it slidingly engages and fits within the inner diameter of tubular member 42. Flange 108 of pull wire 40 must be greater than the inner diameter of tubular member 42, but less than the inner diameter of the lumen of the tubular lead or catheter that is to be removed, and more preferably yet less than or equal to dimension "A" of tubular member 42.

Axial dimension "C" in FIG. 9 is the length of aperture 49, and ranges between about 0.5 and about 5 times dimension "A", between about 1.0 and about 4 times dimension "A", or between about 1.5 and about 3 times dimension "A". In preferred embodiments of the present invention, dimension "C" ranges between about 1 and about 3 times dimension "A".

Radial dimension "D" in FIG. 9 is the depth of aperture 49, and ranges between about ⅓ and about 9/10 of dimension "A", between about ½ and about ⅞ of dimension "A", or between about ⅔ and about ¾ of dimension "A". One purpose of aperture 49 is to decrease the column failure strength of tubular member 42 such that the tensile strength of pull wire 40 exceeds the column failure strength of tubular member 42 at a predetermined location, most preferably in a region propinquant to aperture 49. In FIG. 9, that predetermined failure location corresponds to the region positioned beneath aperture 49 designated generally with reference numeral 106.

FIG. 9 shows pull wire 40 affixed to tubular member 42 at the extreme distal end thereof. Several different methods for achieving such a fixed connection are contemplated in the present invention. One method depicted in FIG. 9 involves flattening wire 40 beyond the extreme distal end of tubular member 42, such that the distal end of wire 40 is prevented from being pulled in a proximal direction into lumen 19 of tubular member 42. Another method for connecting wire 40 to tubular member 42 involves crimping or laser welding generally in the area designated with reference numeral 100 in FIG. 9.

Locking stylet 12 is provided with manipulable handle assembly 44 or other tractional force imparting mechanism or means for providing proximally-directed tractional force on pull wire 40 with respect to tubular member 42. This force is directed in the direction of arrow 102 in FIG. 10. When such force is applied to wire 40, the fixed connection of the distal ends of wire 40 and tubular member 42, in cooperation with aperture 49 spaced back slightly from the distal end of tubular member 42, permits tubular member 42 to deform permanently, bend sharply or kink in an area designated generally with reference numeral 106 in FIG. 9.

Figure 11:
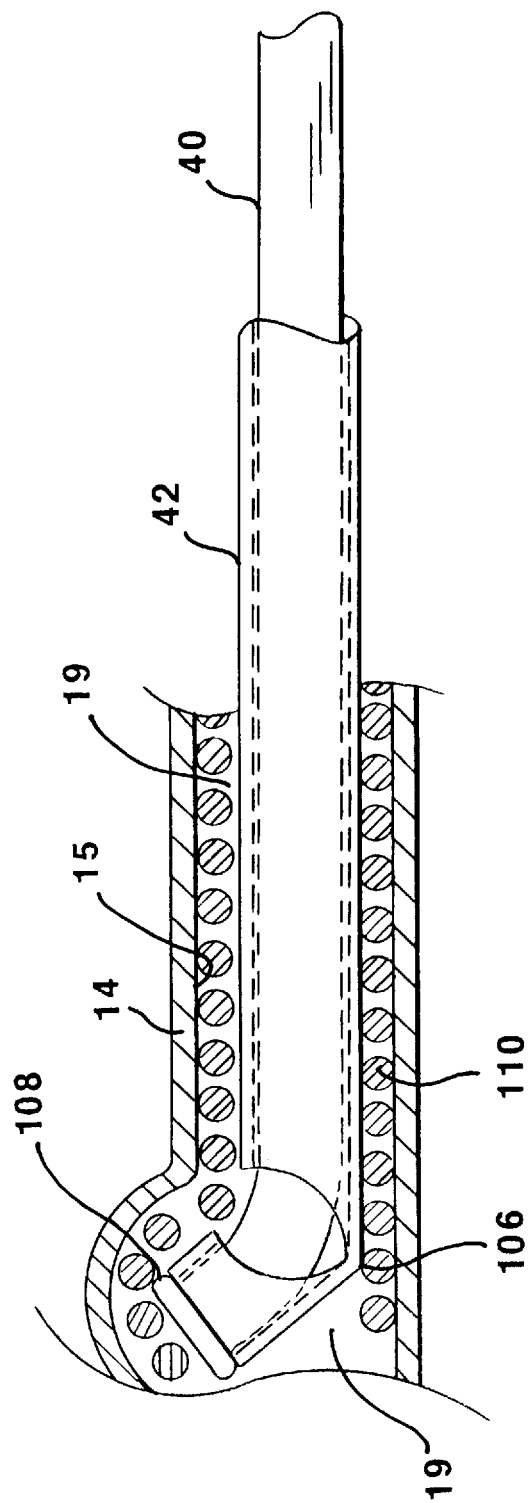
FIG. 11 is an enlarged cross-sectional view of a distal portion of the locking stylet from FIG. 2 in an articulated position within a distal portion of a body-implantable lead.

FIGS. 10 and 11 show distal end 42 of locking stylet 12 after it has become permanently deformed, sharply bent or kinked in accordance with the teachings of the present invention. A user must manipulate the tractional force imparting mechanism to impart at least a predetermined amount of tractional force to the proximal end of the pull-wire 40 such that distal end 42 is permanently deformed, sharply bent or kinked at or near location 106 and portions of distal end 42 near location 108 forcibly engage inner sidewall 15 of lumen 19 or filars 110. The foregoing predetermined amount of force roughly equals the column failure strength of tubular member 42 near aperture 49 or location 106.

As shown in FIG. 10, distal end 48 of locking stylet 12, which previously had a maximum cross-sectional dimension "A" now has a larger maximum cross-sectional dimension designated as dimension "B". This increase in maximum cross-sectional dimension enables stylet 12 to forcibly engage distal conductor filars 110 of coiled-conductor body-implantable lead body or catheter body 14.

The engagement of locking stylet 12 with filars 110 of coiled-conductor lead or catheter body 14 may be best appreciated with reference to the cross-sectional view of FIG. 11. When stylet 12 is inserted in lumen 19 of lead body or catheter body 14 and pull-wire 40 is actuated or pulled by a user to form the permanently deformed, sharply bent, or kinked portion of distal end 48 shown in FIG. 11 near or at location 106, stylet 12 engages lead body or catheter body 14 at the points designated with reference numerals 106 and 108. Tubular member 42 and pull-wire 40 may then be withdrawn together to extract lead 10 from the patient.

As a result of the force applied by distal end 48 to inner sidewalls 15 of lumen 19 of lead body or catheter body 14, stylet 12 may locally deform lead body or catheter body 14 at locations 106 or 108 to such an extent that the resulting local deformation is visible to the eye on the exterior, outer surface of lead or catheter 10. Conversely, stylet 12 may locally deform lead body or catheter body 14 to such an extent that the resulting local deformation is not visible to the eye and indeed may only extend to portions of inner sidewall 15 propinquant to lumen 19.

It is a requirement of the present invention that dimension "B" be greater than or equal to dimension "A". Distal end 48 of stylet 12 need not engage members such as coils 110 to function properly, but may engage the polymeric or other inner sidewall 15 of lead or catheter 10, be it formed of polymeric material or other suitable biocompatible material.

The universal aspect of the locking stylet of the present invention may best be appreciated with reference to FIG. 11. (By "universal" we mean that the disclosed locking stylet may be advantageously employed to extract various types and sizes of leads.) Because the extent to which distal end 48 of locking stylet 12 is permanently deformed, sharply bent or kinked, and consequently the extent to which the cross-sectional dimension of distal end 48 increases, depends upon the extent to which pull wire 40 is pulled back, a single size stylet 12 may be advantageously employed used for extracting leads having a relatively wide range of lumen dimensions.

Of course, the size of stylet 12 may be optimized for use in conjunction with leads having lumens of particular sizes or diameters. The sizes of leads which may be extracted by a single size embodiment of lead 12 varies over a significant range. Stylet 12 is therefore advantageously not limited to use in conjunction with a single size or type of lead. The present invention advantageously permits tractional force to be applied near the distal end of lead 10, and thereby avoids the above-noted problems respecting simply pulling lead 10 out by its proximal end.

FIGS. 12, 13, 14 and 15 depict another embodiment of the present invention, where manipulable handle assembly is designated generally with reference numeral 44'. (It is to be understood that those components of FIGS. 12 through 15 which are identical to counterparts described above with reference to FIGS. 1–11 have retained identical reference numerals in FIGS. 12–15.) Like manipulable handle assembly 44 shown in FIGS. 2 through 11, manipulable handle assembly 44' is adapted to apply proximally-directed tractional force upon pull wire 40 of locking stylet 12, thereby causing the above-described permanent deformation, sharp bending or kinking at the distal end thereof.

FIG. 12 shows that manipulable handle assembly 44' comprises two primary components: an outer, substantially hollow cylindrical shell 150 and an inner, substantially cylindrical insert 152. As will be hereinafter described in further detail, insert 152 is threadably engaged within cylindrical shell 150 such that insert 152 may be screwed into and out of shell 150. Socket 154 projects forwardly from the distal end of shell 150. Socket 154 has a substantially cylindrical lumen 156 extending longitudinally therein. In accordance with one aspect of the invention, lumen 156 is sized such that it permits tubular member 42 of locking stylet to be inserted therein. However, a shoulder 162 is provided on the proximal end of lumen 156, such that tubular member 42 is prevented from passing completely through lumen 156. Thin slot 157 is formed in socket 154 such that pull wire 40, but not tubular member 42, may be pulled or fit therethrough.

Figure 14:
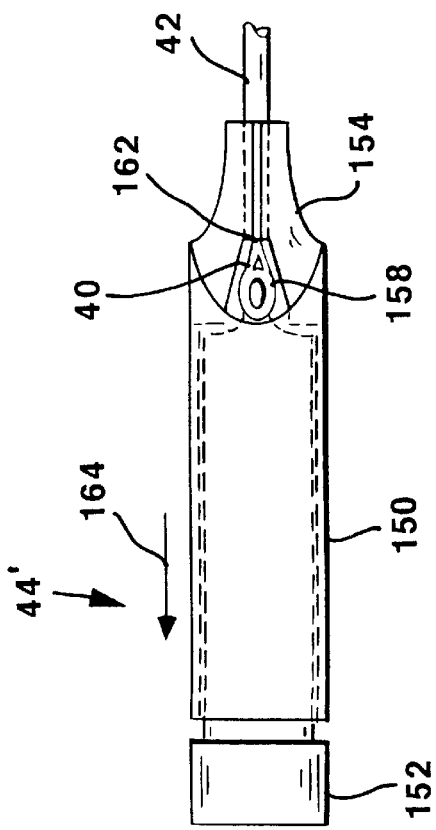
FIG. 14 is a top view of the manipulable handle assembly from FIG. 12 operatively coupled to the locking stylet of FIG. 2.
Figure 15:
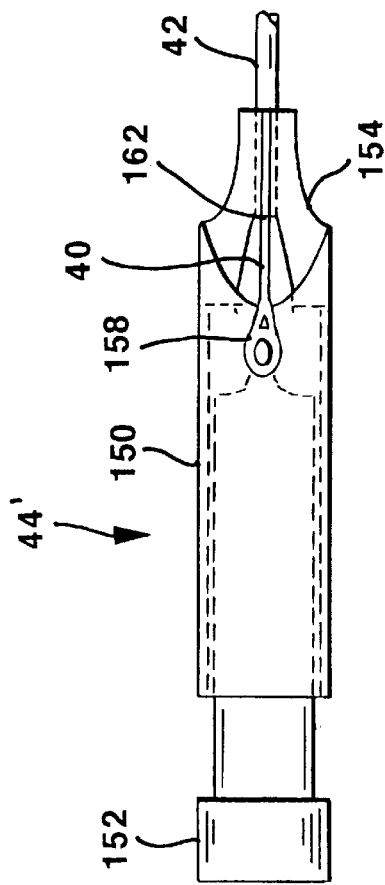
FIG. 15 is a top view of the manipulable handle assembly from FIG. 12 after application of tractional force to the pull wire of the locking stylet of FIG. 2.

In the embodiment of the present invention shown in FIGS. 12 through 15, pull wire 40 is preferably provided with a loop 158 at its proximal end. Loop 158 is adapted to be engaged over a knob or hook element 160 disposed on the distal end of threaded insert 152. Manipulable handle assembly 44' is operatively coupled to locking stylet 12 as follows. After stylet 12 has been inserted into the lumen of a lead to be retracted, pull wire 40 is laid into lumen 156 via slot 157 (see FIG. 12) and tubular member 42 is inserted into lumen 156 from the distal end of handle assembly 44' until it abuts shoulder 162, as shown in FIG. 14. Loop 158 on pull wire 40 is then placed over knob 160, as also shown in FIG. 14.

With manipulable handle assembly 44' so coupled to stylet 12, proximally directed tractional force is applied to pull wire 40, while tubular member 42 is held stationary, by rotating or screwing-out insert 152 from shell 150. The threadable engagement of insert 152 within shell 150 is such that as insert 152 is rotated in one direction (e.g., counterclockwise) with respect to shell 150, insert 152 is drawn proximally out of shell 150 (i.e., in the direction of arrow 164 in FIG. 14) to a retracted position shown in FIG. 15. As a result of pull wire 40 being engaged onto knob 160, and of tubular member 142 being prevented from being drawn completely through groove 156 by shoulder 162, proximally-directed tractional force is applied to pull wire 40 while tubular member 42 is held stationary. This causes the above-described kinking, bending or deformation at the distal end of stylet 12.

Those of ordinary skill in the art will appreciate that the pitch of threads provided for the threaded engagement of insert 152 within shell 150 may be made very slight to afford a high mechanical advantage with respect to the tractional force applied to pull wire 40. Thus, a considerable force can be applied to pull wire 40 even though rotating or unscrewing insert 152 with respect to shell 150 is relatively easy.

Figure 16:
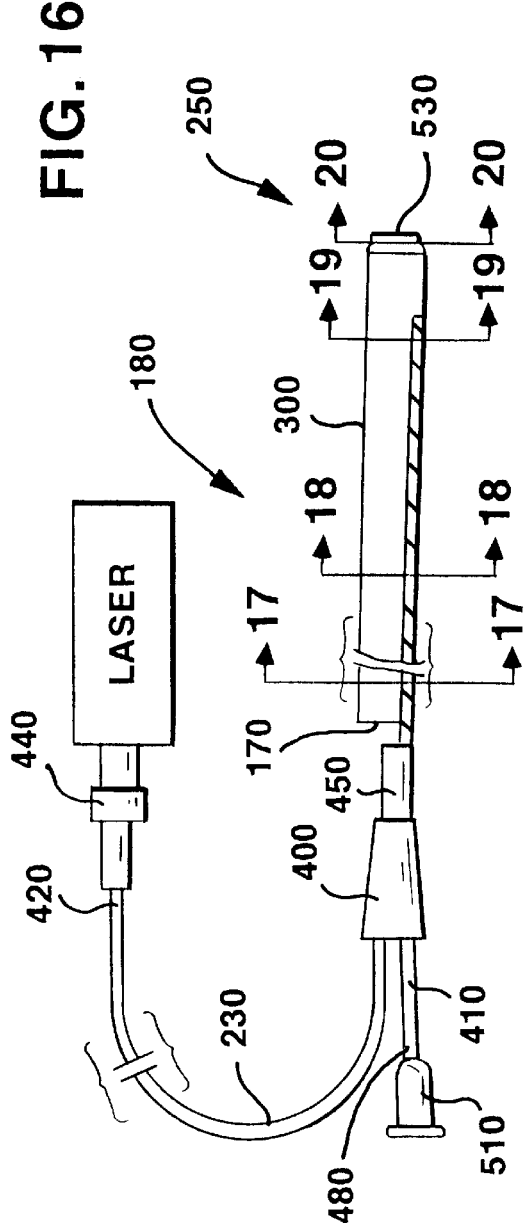
FIG. 16 is a plan view of an implanted object extractor constructed according to the present invention.

FIG. 16 depicts a plan view of catheter 180. FIGS. 16 through 19 show various plan and cross-sectional views of catheter 180. As seen, catheter 180 comprises catheter body 300, bifurcate cover 400 and stylet leg 410 extending therefrom, and at least one optical fiber 230. The optical fiber or fibers 230 used are preferably a 130 micron fiber available from the Spectranetics Corporation in Colorado Springs, Colo., USA. The specific optical fibers used, however, are not within the scope of the claimed invention and any optical fiber suitable to transmit laser energy to ablate fibrous scar tissue may be used. Located at proximal end 420 of optical fibers 230 sits coupler 440. Coupler 440 permits optical fibers 230 to be coupled to a laser light energy source (not shown.) The laser light energy source is preferably a xenon-chloride laser such as Model No. CVX-300 available from the Spectranetics Corporation discussed above. Coupler 440 may be of any configuration known in the art. A suitable coupler 440 may also be obtained from Spectranetics Corporation. Bifurcate cover 400 cooperates with skirt 450 to feed optical fibers 230 into catheter body 300 as well as stylet leg 410 into stylet tube 500 in catheter body 300. Proximal end 480 of stylet leg 410 has stylet introducer 510.

Catheter body 300 shown in cross section in FIGS. 17 through 20 has guide lumen 310 running therethrough and is preferably constructed from a biocompatible material such as polyurethane. Positioned within catheter body 300 are optical fibers 230 and stylet tube 500. Stylet tube 500 permits a stylet to be introduced through catheter body 300 and thereby move catheter 180 through the venous system. In a preferred embodiment a steerable stylet may be used with the disclosed invention, such as the steerable stylet disclosed in U.S. patent application Ser. No. 08/069,310 to Brennan et al. entitled "Steerable Stylet and Manipulative Handle Assembly" filed May 28, 1993, incorporated herein by reference. Additionally a lead extender (not shown) may be provided to permit traction to be applied along lead throughout guide lumen 310. Specifically the lead extender would be attached to lead 200 and passed from distal end 250 of catheter 180 through guide lumen 310 and exiting at proximal end 170 of catheter body 300. Extender may be any suitable object, such as a suture or wedging stylet, which may be attached to lead and passed through guide lumen 310 to permit the application of traction to lead.

Figure 20:
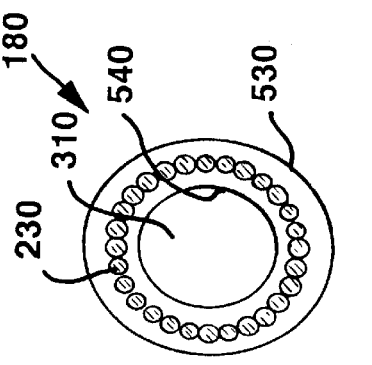
FIG. 20 is a sectional view of the device shown in FIG. 16 taken along the lines 20—20.
Figure 19:
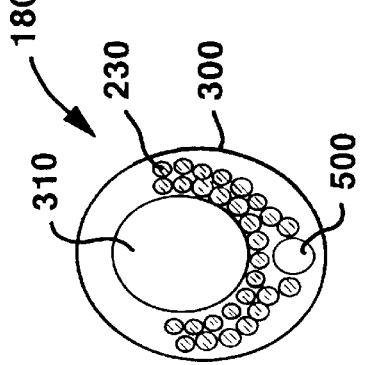
FIG. 19 is a sectional view of the device shown in FIG. 16 taken along the lines 19—19.
Figure 18:
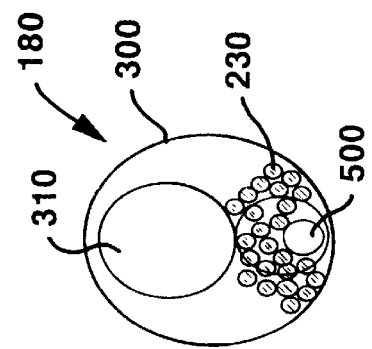
FIG. 18 is a sectional view of the device shown in FIG. 16 taken along the lines 18—18.
Figure 17:
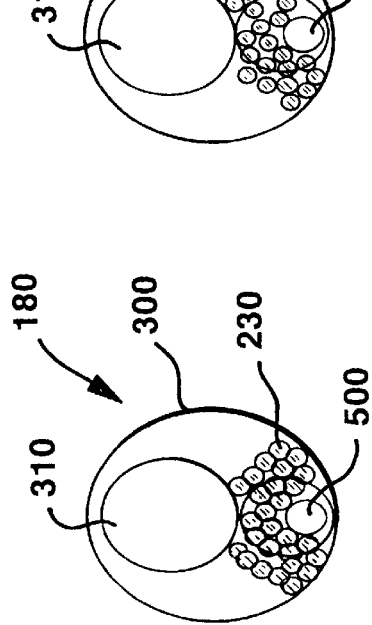
FIG. 17 is a sectional view of the device shown in FIG. 16 taken along the lines 17—17.
Figure 21:
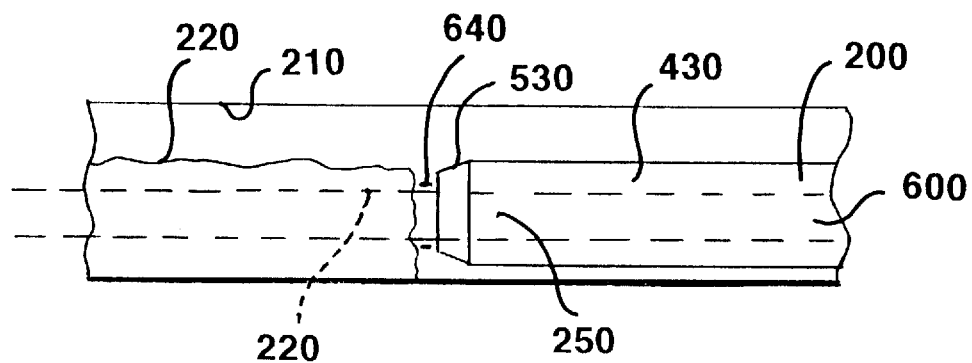
FIG. 21 is a side plan detail view of the distal portion of the implanted object extractor of FIG. 16 as it would be used to remove a lead.
Figure 22:
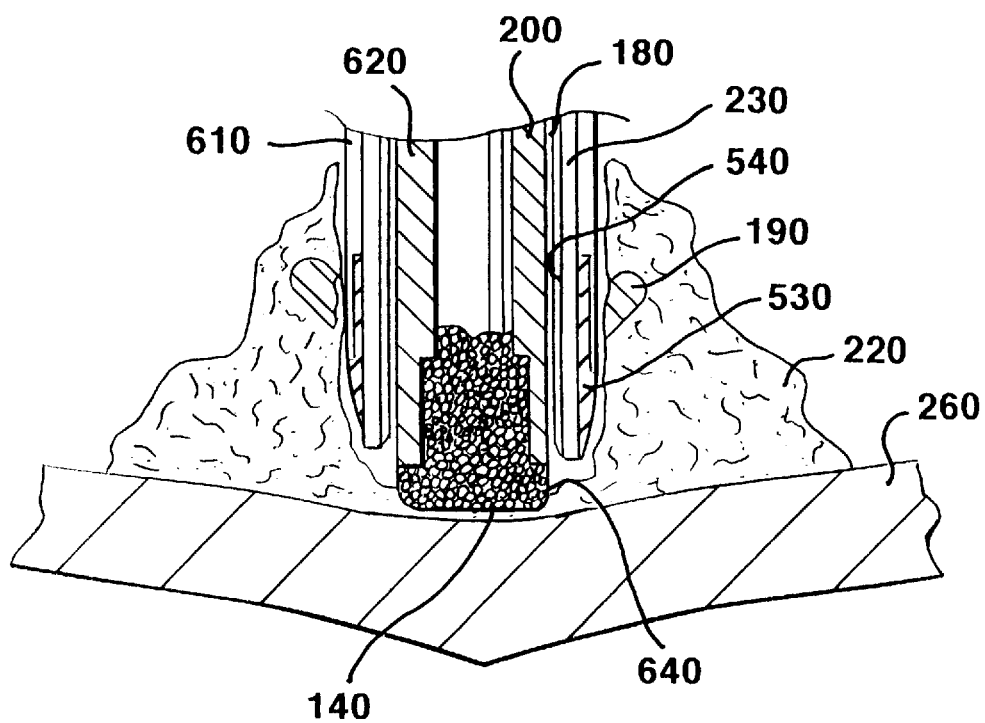
FIG. 22 is a side sectional view of the distal portion of an implanted lead showing a laser extractor for an implanted object of the present invention removing fibrous scar tissue.

As shown in FIGS. 19 through 20, optical fibers 230 are positioned within catheter body 300 in a preferred annular arrangement at distal end 250 of catheter 180. Optical fibers 230 are arranged in an annular configuration to permit laser light energy 640 to be emitted onto fibrous scar tissue 220 that encapsulates, is disposed along or is affixed to lead 200. Laser light energy ablates such scar tissue 200 as shown in FIGS. 21 and 22, and thereby permits lead 200 to be freed and removed from a patient's body. Optical fiber may also be arranged in an annular configuration throughout the length or a portion of catheter body 300 to decrease the overall diameter of catheter body 300 and to increase the overall ability of catheter body 300 to be pushed along lead 200. Moreover, optical fibers 230 may also be incorporated as one fiber throughout the length or a portion of catheter body 300 and then separate or bifurcate in an annular configuration around distal end 250.

FIG. 22 shows the distal end of lead 200 embedded in fibrous scar tissue formed on a substrate of tissue 260. Optical fibers 230 are disposed between external catheter sidewall 530 and internal catheter sidewall 540. Lead insulative sleeve 620 is propinqaunt to internal catheter sidewall 540. Operation of catheter 180 to extract lead 200 is as follows. The proximal end of lead 200 is uncovered surgically so that catheter 180 may be introduced thereover. Next, the proximal end of lead 200 is introduced into guide lumen 310. If required, this step may be accomplished by removing the connector pin assembly from proximal end of lead 200, affixing an extender which extends through guide lumen 310 to lead 200, and introducing lead 200 within guide lumen 310. Once catheter 180 is positioned so lead 200 extends through guide lumen 310, catheter 180 is moved until distal end 250 of catheter 180 is proximate fibrous scar tissue 220.

As shown in FIG. 21, laser light energy 640 from a laser (not shown) is transmitted through optical fibers 230 and onto fibrous scar tissue 220, thereby ablating fibrous scar tissue 220 and releasing lead 200 in the area proximate distal end 250 of catheter 180. Catheter 180 is repositioned until once again distal end 250 of catheter 180 is proximate fibrous scar tissue 220. Transmission of laser light energy 640 onto fibrous scar tissue 220 is repeated along the entire length of lead 200 until lead 200 is no longer affixed by fibrous scar tissue 220 along its side surface 220. As seen in FIG. 22 laser light energy 640, besides ablating fibrous scar tissue 220, also ablates and cuts through tines 190, particularly if tines 190 are constructed from common lead materials, such as silicone or polyurethane.

As shown in FIG. 22, once side surface 220 of lead 200 is released from fibrous scar tissue 220, only fibrous scar tissue proximate distal end 250 of lead 200 at distal face of electrode 140 retains lead 200. At this point traction may be applied to either proximal end of lead 200 or to a point proximal distal end of lead 200, such as through a snagging stylet of the type disclosed in U.S. Pat. Nos. 5,207,683, 5,013,310, 4,988,347 and 4,943,289 to Goode et al. Lead 200 is then withdrawn from fibrous scar tissue 220 and removed from the patient. Use may also be made of a sheath, such as that disclosed in U.S. Pat. No. 5,011,482 to Goode et al., to overlay lead 200 during traction and apply counter traction at a site near the electrode to confine the tractional force to a small area within the sheath.

It will now be appreciated be those of ordinary skill in the art that the present invention is not directed to a stylet that imparts steerability to a catheter or lead, but instead to a stylet that is capable of applying tractional force to the distal end of an implanted lead or catheter and removing the lead or catheter from a patient, where the lead or catheter has a lumen accessible to the tubular member or stylet of the present invention. The present invention permits the extraction of such catheters or leads through the application of a relatively large engagement force to the distal end of the lead or catheter via a pull wire and the permanent deformation, sharp bending or kinking of the distal end of the tubular member of the present invention against the sidewall of the lumen of the lead or catheter to be removed.

Moreover, unlike many known tractional force imparting mechanisms of the prior art, the stylet or tubular member of the present invention may be employed to remove any implanted lead or catheter having a lumen disposed therewithin, wherein the inner diameter of the lumen exceeds dimension "A" of the present invention. Thus, a single size stylet 12 of the present invention may be employed to remove leads or catheters having a relatively wide range of lumen diameters. This advantage of the present invention eliminates the requirement for having an array of different stylets having very precise yet different dimensions available during a lead or catheter surgical removal procedure.

A method of using the present invention will now be described. After a patient has been appropriately prepared for a lead or catheter surgical removal procedure, a surgeon dissects the patient's flesh to the extent required to reveal the proximal end of the implanted catheter or lead. The proximal end of the catheter or lead is removed from the IPG, drug pump or other device to which it is attached, and the universal locking stylet 12 of the present invention is threaded down inside suitable lumen 19 thereof. When the distal end 48 of stylet 12 has reached the most distal portion or end of the implanted lead or catheter, the locking mechanism of the present invention is actuated by applying tractional force to pull wire 40 such that distal end 48 engages locations 106 and 108 of lumen 19 of the lead or catheter to be removed. Additional tractional force may now be imparted to pull wire 40 and stylet 12 to remove the implanted lead or catheter from the patient.

From the foregoing detailed description of a preferred embodiment of the invention, it should be apparent that a universal locking stylet for facilitating the extraction of body-implantable leads and the like has been described. Although a particular embodiment of the invention has been described herein in some detail, it is to be understood that this has been done solely for the purposes of illustrating the invention in various of its aspects. It is contemplated that various substitutions, alterations, and/or modifications, including but not limited to those specifically discussed herein, may be made to the disclosed embodiment without departing from the spirit and scope of the invention as defined in the appended claims, which follow.

For example, although a particular configuration for the manipulable handle 44 of locking stylet 12 has been proposed herein, it is contemplated that various other means and handles may be devised for applying tractional force to wire 40 with respect to tubular member 42 that would fall within the scope of the present invention as claimed herein. While various dimensions of stylet 12 have been stated herein, it is to be understood that such dimensions may vary depending upon particular applications of the invention. Different biocompatible and otherwise suitable materials other than those set forth herein may also be employed to form stylet 12 or pull wire 40.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All U.S. Patents listed in this document are hereby incorporated into the specification hereof in their respective entireties.

We claim:

1. A locking stylet for extraction of an elongate, body-implantable lead or catheter, the lead or catheter having a first lumen disposed therewithin, the first lumen having distal and proximal ends, the locking stylet comprising:

an elongate, flexible tubular member having a first length and a second lumen defined by inner sidewalls, the tubular member having proximal and distal ends, the tubular member further having an outer diameter "A" defined by outer sidewalls, the outer diameter being sufficiently small to be received within the first lumen, the tubular member having an aperture formed proximally, propinquant to and a distance "E" from the distal end thereof, the aperture having an axial length "C" and a radial depth "D", the aperture extending through and between the outer sidewalls and the inner sidewalls;

a pull-wire having a second length and proximal and distal ends, the pull-wire being disposed at least partially within the second lumen, the distal end of the pull-wire being affixed to or engaging the distal end of the tubular member, the second length exceeding or equalling the first length, the pull-wire extending along at least the entire first length, and a tractional force imparting mechanism coupled to the proximal end of the pull wire, the tractional force imparting mechanism being adapted to apply proximally-directed tractional force to the pull-wire;

wherein when the tractional force imparting mechanism is manipulated by a user to impart at least a predetermined amount of tractional force to the proximal end of the pull-wire, the distal end of the pull wire causes a first portion of the distal end of the tubular member to sharply bend in a region located propinquant to the aperture such that at least a second portion of the distal end of the tubular member forcibly engages and locally deforms at least a portion of an inner sidewall of the first lumen.

2. The stylet of claim 1, wherein dimension "A" ranges between about 0.75 inches and about 0.006 inches.

3. The stylet of claim 1, wherein dimension "A" ranges between about 0.50 inches and about 0.010 inches.

4. The stylet of claim 1, wherein dimension "A" ranges between about 0.25 inches and about 0.012 inches.

5. The stylet of claim 1, wherein dimension "A" ranges between about 0.20 inches and about 0.14 inches.

6. The stylet of claim 1, wherein dimension "A" ranges between about 0.18 inches and about 0.15 inches.

7. The stylet of claim 1, wherein dimension "A" is about 0.016 inches.

8. The stylet of claim 1, wherein dimension "E" ranges between about 0.006 and about 1.0 inch.

9. The stylet of claim 1, wherein dimension "E" ranges between about 0.010 and about 0.50 inches.

10. The stylet of claim 1, wherein dimension "E" ranges between about 0.012 and about 0.30 inches.

11. The stylet of claim 1, wherein dimension "E" ranges between about 0.014 inches and about 0.110 inches.

12. The stylet of claim 1, wherein dimension "E" ranges between about 0.016 inches to about 0.075 inches.

13. The stylet of claim 1, wherein dimension "E" ranges between about 0.018 inches and about 0.050 inches.

14. The stylet of claim 1, wherein dimension "E" ranges between about between about 0.020 inches and about 0.042 inches.

15. The stylet of claim 1, wherein dimension "E" ranges between about 0.016 inches and about 0.042 inches.

16. The stylet of claim 1, wherein the ratio of dimension "E" to dimension "A" ranges between about ⅛ and about 3.

17. The stylet of claim 1, wherein the ratio of dimension "E" to dimension "A" ranges between about ¼ and about 2.

18. The stylet of claim 1, wherein the ratio of dimension "E" to dimension "A" ranges between about ½ and about 1.

19. The stylet of claim 1, wherein the ratio of dimension "E" to dimension "A" ranges between about 1 and about 3.

20. The stylet of claim 1, wherein the ratio of dimension "C" to dimension "A" ranges between about 0.5 and about 5.

21. The stylet of claim 1, wherein the ratio of dimension "C" to dimension "A" ranges between about 1 and about 4.

22. The stylet of claim 1, wherein the ratio of dimension "C" to dimension "A" ranges between about 1 and about 4.

23. The stylet of claim 1, wherein the ratio of dimension "C" to dimension "A" ranges between about 1.5 and about 3.

24. The stylet of claim 1, wherein the ratio of dimension "C" to dimension "A" ranges between about 1 and about 3.

25. The stylet of claim 1, wherein the ratio of dimension "D" to dimension "A" ranges between about ⅓ and about 9/10.

26. The stylet of claim 1, wherein the ratio of dimension "D" to dimension "A" ranges between about ½ and about ⅞.

27. The stylet of claim 1, wherein the ratio of dimension "D" to dimension "A" ranges between about ⅔ and about ¾.

28. The stylet of claim 1, wherein a column failure strength of the tubular member in a region propinquant to the aperture is less than a tensile strength of the pull wire.

29. The stylet of claim 1, wherein the pull wire is formed of chromium-nickel alloy.

30. The stylet of claim 1, wherein the pull wire has a diameter of about 0.007-inches.

31. The stylet of claim 1, wherein the tubular member is formed of stainless steel tubing.

32. The stylet of claim 1, wherein the proximal end of the pull-wire extends beyond the proximal end of the tubular member.

33. The stylet of claim 1, wherein the stylet is universal.

34. The stylet of claim 1, wherein the tractional force imparting mechanism is a manipulable handle assembly.

35. The stylet of claim 1, wherein the tubular member normally has a substantially uniform outer diameter "A".

36. The stylet of claim 1, wherein the tubular member assumes an outer diameter "B" upon application of a predetermined amount of force by a user to the tractional force imparting mechanism.

37. A method of extracting an elongate body-implantable lead or catheter from a patient, the lead or catheter having a first lumen, the first lumen having distal and proximal ends, comprising the steps of:

(a) inserting into the first lumen an elongate tubular member, the tubular member having a second lumen, proximal and distal ends and inner and outer sidewalls, the proximal end of the tubular member being connected to a tractional force imparting mechanism, a pull-wire having proximal and distal ends being disposed within the second lumen and extending between the proximal and distal ends of the tubular member, the proximal end of the pull-wire being affixed to the tractional force mechanism, the distal end of the pull wire being connected to or engaging the distal end of the tubular member, the tubular member further having a normally substantially uniform outer diameter defined by outer sidewalls, the outer diameter being sufficiently small to be received within the first lumen;

(b) applying, with the tractional force imparting mechanism, a first tractional force to the pull wire, the first tractional force being transferred to the distal end of the pull wire and thence to the distal end of the tubular member, the first force causing a first portion of the tubular member to sharply bend in a region propinquant to an aperture such that at least a second portion of the distal end of the tubular member forcibly engages and locally deforms at least a portion of an inner sidewall of the first lumen, and (c) extracting the pull wire, tubular member and lead or catheter from the patient by applying a second tractional force to a combined assembly comprising the tractional force mechanism, the pull wire, the tubular member and the lead or catheter.

38. A system for extracting an elongate implanted lead or catheter from a human or other mammalian subject, the lead or catheter having a first lumen disposed therewithin, the first lumen having distal and proximal ends, the system comprising:

(a) means for separating body tissue from the implanted object;

(b) a locking stylet, comprising:

(1) an elongate, flexible tubular member having a first length and a second lumen defined by inner sidewalls, the tubular member having proximal and distal ends, the tubular member further having an outer diameter "A" defined by outer sidewalls, the outer diameter being sufficiently small to be received within the first lumen, the tubular member having an aperture formed proximally, propinquant to and a distance "E" from the distal end thereof, the aperture having an axial length "C" and a radial depth "D", the aperture extending through and between the outer sidewalls and the inner sidewalls;

(2) a pull-wire having a second length and proximal and distal ends, the pull-wire being disposed at least partially within the second lumen, the distal end of the pull-wire being affixed to or engaging the distal end of the tubular member, the second length exceeding or equalling the first length, the pull-wire extending along at least the entire first length, and (3) a tractional force imparting mechanism coupled to the proximal end of the pull wire, the tractional force imparting mechanism being adapted to apply proximally-directed tractional force to the pull-wire;

wherein when the tractional force imparting mechanism is manipulated by a user to impart at least a predetermined amount of tractional force to the proximal end of the pull-wire, the distal end of the pull wire causes a first portion of the distal end of the tubular member to sharply bend in a region located propinquant to the aperture such that at least a second portion of the distal end of the tubular member forcibly engages and locally deforms at least a portion of an inner sidewall of the first lumen;

and wherein the body tissue separating means is optionally employed to remove scar tissue from around the distal end of the implanted lead or catheter before the locking stylet is employed to sharply bend the distal end of the tubular member.

39. The system of claim 38, wherein the means for separating body tissue from the distal end of the implanted lead or catheter is a laser catheter.

40. The system of claim 38, wherein the means for separating body tissue from the distal end of the implanted lead or catheter is a cutting catheter.

41. Means for extracting an elongate, body-implantable lead or catheter, the lead or catheter having a first lumen disposed therewithin, the first lumen having distal and proximal ends, the extracting means comprising:

elongate, flexible tubular means for accepting a pulling means, the elongate, flexible tubular means having a first length and a second lumen defined by inner sidewalls, the tubular means having proximal and distal ends, the tubular means further having an outer diameter "A" defined by outer sidewalls, the outer diameter being sufficiently small to be received within the first lumen, the tubular means having means for structurally failing formed proximally, propinquant to and a distance "E" from the distal end of the tubular means, the failing means having an axial length "C" and a radial depth "D", the failing means forming a hole extending through and between the outer sidewalls and the inner sidewalls;

means for pulling the distal end of the tubular means, the pulling means having a second length and proximal and distal ends, the pulling means being disposed at least partially within the second lumen, the distal end of the pulling means being affixed to or engaging the distal end of the tubular means, the second length exceeding or equalling the first length, the pulling means extending along at least the entire first length, and means for imparting a tractional force to the pulling means, the tractional force imparting means being coupled to the proximal end of the pulling means, the tractional force imparting means being adapted to apply proximally-directed tractional force to the pulling means;

wherein when the tractional force imparting means is manipulated by a user to impart at least a predetermined amount of tractional force to the proximal end of the pulling means, the distal end of the pulling means causes a first portion of the distal end of the tubular means to sharply bend in a region located propinquant to the failing means such that at least a second portion of the distal end of the tubular means forcibly engages and locally deforms at least a portion of an inner sidewall of the first lumen.

42. The extracting means of claim 41, wherein dimension "A" ranges between about 0.75 inches and about 0.006 inches.

43. The extracting means of claim 41, wherein dimension "A" ranges between about 0.50 inches and about 0.010 inches.

44. The extracting means of claim 41, wherein dimension "A" ranges between about 0.25 inches and about 0.012 inches.

45. The extracting means of claim 41, wherein dimension "A" ranges between about 0.20 inches and about 0.14 inches.

46. The extracting means of claim 41, wherein dimension "A" ranges between about 0.18 inches and about 0.15 inches.

47. The extracting means of claim 41, wherein dimension "A" is about 0.016 inches.

48. The extracting means of claim 41, wherein dimension "E" ranges between about 0.006 and about 1.0 inch.

49. The extracting means of claim 41, wherein dimension "E" ranges between about 0.010 and about 0.50 inches.

50. The extracting means of claim 41, wherein dimension "E" ranges between about 0.012 and about 0.30 inches.

51. The extracting means of claim 41, wherein dimension "E" ranges between about 0.014 inches and about 0.10 inches.

52. The extracting means of claim 41, wherein dimension "E" ranges between about 0.016 inches to about 0.075 inches.

53. The extracting means of claim 41, wherein dimension "E" ranges between about 0.018 inches and about 0.050 inches.

54. The extracting means of claim 41, wherein dimension "E" ranges between about between about 0.020 inches and about 0.042 inches.

55. The extracting means of claim 41, wherein dimension "E" ranges between about 0.016 inches and about 0.042 inches.

56. The extracting means of claim 41, wherein the ratio of dimension "E" to dimension "A" ranges between about ⅛ and about 3.

57. The extracting means of claim 41, wherein the ratio of dimension "E" to dimension "A" ranges between about ¼ and about 2.

58. The extracting means of claim 41, wherein the ratio of dimension "E" to dimension "A" ranges between about ½ and about 1.

59. The extracting means of claim 41, wherein the ratio of dimension "E" to dimension "A" ranges between about 1 and about 3.

60. The extracting means of claim 41, wherein the ratio of dimension "C" to dimension "A" ranges between about 0.5 and about 5.

61. The extracting means of claim 41, wherein the ratio of dimension "C" to dimension "A" ranges between about 1 and about 4.

62. The extracting means of claim 41, wherein the ratio of dimension "C" to dimension "A" ranges between about 1 and about 4.

63. The extracting means of claim 41, wherein the ratio of dimension "C" to dimension "A" ranges between about 1.5 and about 3.

64. The extracting means of claim 41, wherein the ratio of dimension "C" to dimension "A" ranges between about 1 and about 3.

65. The extracting means of claim 41, wherein the ratio of dimension "D" to dimension "A" ranges between about $1/3$ and about $9/10$.

66. The extracting means of claim 41, wherein the ratio of dimension "D" to dimension "A" ranges between about $1/2$ and about $7/8$.

67. The extracting means of claim 41, wherein the ratio of dimension "D" to dimension "A" ranges between about $2/3$ and about $3/4$.

68. The extracting means of claim 41, wherein the column failure strength of the tubular means in a region propinquant to the failing means is less than the tensile strength of the pulling means.

69. The extracting means of claim 41, wherein the pulling means is formed of chromium-nickel alloy.

70. The extracting means of claim 41, wherein the pulling means has a diameter of about 0.007-inches.

71. The extracting means of claim 41, wherein the tubular means is formed of stainless steel tubing.

72. The extracting means of claim 41, wherein the proximal end of the pulling means extends beyond the proximal end of the tubular means.

73. The extracting means of claim 41, wherein the extracting means is universal.

74. The extracting means of claim 41, wherein the tractional force imparting means is a manipulable handle assembly.

75. The extracting means of claim 41, wherein the tubular means normally has a substantially uniform outer diameter "A".

76. The extracting means of claim 41, wherein the tubular means assumes an outer diameter "B" upon application of a predetermined amount of force by a user to the tractional force imparting means.

* * * * *

UNITED STATES PATENT AND TRADEMARK OFFICE
CERTIFICATE OF CORRECTION

PATENT NO. : 5,769,858

DATED : June 23, 1998

INVENTOR(S) : Robert M. Pearson, Thomas C. Bischoff; Brian Lee Fideler

It is certified that error appears in the above-identified patent and that said Letters Patent is hereby corrected as shown below:

Column 15, Line 35: "and about 0.110 inches: should be "and about 0.10 inches"

Signed and Sealed this

Twenty-eighth Day of November, 2000

Attest:

Q. TODD DICKINSON

Attesting Officer

Director of Patents and Trademarks